(12) United States Patent
Clausen (10) Patent No.: US 7,195,697 B2
(45) Date of Patent: Mar. 27, 2007

(54) SENSOR MEMBRANE, A METHOD FOR THE PREPARATION THEREOF, A SENSOR AND A LAYERED MEMBRANE STRUCTURE FOR SUCH SENSOR

(75) Inventor: Lydia Clausen, Lynge (DK)

(73) Assignee: Radiometer Medical A/S, Bronshoj (DK)

( * ) Notice: Subject to any disclaimer, the term of this patent is extended or adjusted under 35 U.S.C. 154(b) by 370 days.

(21) Appl. No.: 10/301,035

(22) Filed: Nov. 21, 2002

(65) Prior Publication Data
US 2003/0070548 A1    Apr. 17, 2003

Related U.S. Application Data

(63) Continuation of application No. PCT/DK01/00358, filed on May 23, 2001.

(30) Foreign Application Priority Data
May 23, 2000 (DK) ............................... 2000 00819

(51) Int. Cl.
*G01N 27/327* (2006.01)
(52) U.S. Cl. ............ 204/403.06; 204/279; 204/403.11; 427/2.11
(58) Field of Classification Search .......... 204/403.06, 204/903.1, 903.11, 279, 295, 296; 210/500.27; 427/2.11; 428/423.1, 480
See application file for complete search history.

(56) References Cited

U.S. PATENT DOCUMENTS

| | | | |
|---|---|---|---|
| 3,912,614 A | | 10/1975 | Spracklen et al. |
| 4,177,126 A | | 12/1979 | Imaki et al. |
| 4,208,280 A | * | 6/1980 | Naylor .................. 562/42 |
| 4,272,328 A | * | 6/1981 | Kim et al. ............. 205/782.5 |
| 4,645,667 A | * | 2/1987 | Hashimoto et al. ...... 424/282.1 |

(Continued)

FOREIGN PATENT DOCUMENTS

JP        2000-65791        3/2000

(Continued)

OTHER PUBLICATIONS

1997 McClutcheon's vol. 1: Emulsifiers & Detergents.*

(Continued)

*Primary Examiner*—Kaj K. Olsen
(74) *Attorney, Agent, or Firm*—Bryan Cave LLP (57) ABSTRACT

A membrane for a sensor, a method for the preparation thereof, a layered membrane structure and a sensor for analytical measurements which require controlled analyte permeability. The membrane, layered structure and sensor may be used for biological, physiological and chemical measurements, however, are especially applicable for electrochemical measurements of glucose, lactate, urea and creatinine. The membrane comprises at least one polymer material, at least one surfactant, and at least one hydrophilic compound in admixture to provide a membrane structure in which micelles of hydrophilic compound lined with thin layers of surfactant are randomly distributed in the bulk polymer of the membrane. Upon conditioning of the membrane a structure of a perculating network of pores lined with surfactant is formed which has excellent permeability properties. The membrane has the additional advantage of a proper adhesion to polymer encapsulant structures. The membrane is prepared from a mixture of at least one polymer material, at least one surfactant, at least one hydrophilic compound and at least one solvent.

64 Claims, 5 Drawing Sheets

U.S. PATENT DOCUMENTS

| | | | |
|---|---|---|---|
| 4,885,077 A | | 12/1989 | Karakelle et al. |
| 4,919,767 A | | 4/1990 | Vadgama et al. |
| 5,034,330 A | * | 7/1991 | Yamori et al. ......... 204/403.11 |
| 5,322,063 A | | 6/1994 | Allen et al. |
| 5,554,339 A | | 9/1996 | Cozzette et al. |
| 5,658,444 A | | 8/1997 | Black et al. |
| 5,932,212 A | * | 8/1999 | Khalaf ...................... 424/94.6 |
| 6,086,748 A | * | 7/2000 | Durst et al. ................. 205/775 |
| 6,214,185 B1 | | 4/2001 | Offenbacher et al. |
| 6,284,194 B1 | * | 9/2001 | Chu ............................ 422/55 |

FOREIGN PATENT DOCUMENTS

| | | |
|---|---|---|
| WO | WO 97/17607 | 5/1997 |
| WO | WO 97/36994 | 10/1997 |
| WO | WO 97/43634 | 11/1997 |
| WO | WO 99 30152 | 6/1999 |

OTHER PUBLICATIONS

2004 McClutcheon's vol. 1: Emulsifiers & Detergents.*

Merriam-Webster's Collegiate Dictionary, 10th Edition, definition of "polymer".*

Hansen, Charles M., "Hansen Solubility Parameters—A User's Handbook," pp. 1-58 (2000).

* cited by examiner

SENSOR MEMBRANE, A METHOD FOR THE PREPARATION THEREOF, A SENSOR AND A LAYERED MEMBRANE STRUCTURE FOR SUCH SENSOR

This application is a continuation of International Application PCT/DK01/00358 filed May 23, 2001.

This invention relates to a sensor membrane, a method for the preparation thereof, a sensor and a layered membrane structure for such sensor, in particular to a sensor membrane for detection of glucose, lactate, urea or creatinine, a method for the preparation thereof, a sensor for detection of glucose, lactate, urea or creatinine and a layered membrane structure for such sensor.

For the determination of biomolecules electrochemical sensors based on amperometric or potentiometric principles may be used.

Glucose is an important example of a biomolecule which can be measured amperometrically. Sensors based on this principle may the used for the determination of the level of lactate and creatinine as well.

The glucose level of blood is an important clinical parameter. In the case of the disease diabetes which is a result of inadequate secreation of the hormone insulin elevated levels of glucose may lead to life threatening metabolic imbalances and alternations in the blood pH. The amperometrical determination of the glucose level of blood is based on the enzymatic oxidation of glucose ($C_6H_{12}O_6$) to gluconic acid ($C_6H_{10}O_6$) or gluconolactone ($C_6H_{12}O_7$) and subsequent detection of the hydrogen peroxide generated. The oxidation of glucose is catalysed by the enzyme glucose oxidase, whereas the hydrogen peroxide formed is electrochemically oxidised at a platinum electrode, the current from said electrode being a measure of the glucose concentration:

The lactate and creatinine determinations are based on similar enzymatic reactions and determination of hydrogen peroxide generated.

Urea is an example of a biomolecule which can be measured potentiometrically. Accordingly a potentiometric sensor may be used based on the enzymatic degradation of urea to ammonium by urease. The ammonium ion is subsequently measured by an ammonium selective electrode:

Both amperometric and potentiometric biosensors usually comprise a multilayered membrane with an outer membrane part facing the sample.

The outer membrane is a porous or permeable polymer membrane which controls the permeation of analyte and other reactants to the enzyme layer. Thus, in a glucose sensor the membrane should control the permeation of the reactants glucose and oxygen.

In the blood, however, the glucose concentration exceeds the oxygen concentration by orders of magnitude. Thus, the main objective of the outer membrane is to reduce the permeation of glucose to the enzyme layer. The same applies for measurements of other biomolecules.

The permeation of glucose across the outer membrane should preferably be fast, i.e. upon exposure to glucose-containing samples the membrane should provide a fast response of the small amount of glucose reaching the enzyme layer. The short response time allows an early and reliable estimate of the equilibrium concentration of glucose, thus providing a fast measurement procedure. Further, the permeation of interfering species like paracetamol and ascorbic acid is reduced as only short exposure to test samples will be needed.

The currently available membranes all suffer from various disadvantages as is described in further detail below.

According to one approach outer membranes are polymer structures with hydrophilic and hydrophobic regions and no macroscopic porosity. Upon exposure to water the hydrophilic regions of such membranes absorb water, thus providing in the swelled structure a permeation path for glucose. Whereas glucose permeates across the hydrophilic regions only, oxygen permeates across the hydrophobic regions as well as across the hydrophilic regions.

An example of this type of membrane is disclosed in U.S. Pat. No. 5,322,063 to Eli Lilly and Co. which discloses a polyurethane membrane. The membrane has hydrophobic regions of "hard" urethane and hydrophilic regions of "soft" poly(ethylene oxide). The permeability properties of the membrane are determined from the balance between "hard" and "soft" segments, as both types of segments are permeable to oxygen, whereas only the "soft" segments are permeable to glucose.

International patent application No. WO 97/17607 to Victoria University of Manchester discloses a membrane of a synthetic polymer material incorporating a surface active agent, also referred to as a surfactant. According to disclosure of WO 97/17607 a preferred polymer material is PVC. Further according to disclosure of WO 97/17607 one group of preferred surface active agents is polyoxyalkylenes, i.e. ethylene oxides and propylene oxides. Thus, Triton X-100 which is a condensate of 4-octylphenol with approx. 10 molecular proportions of ethylene oxide is an example of such ethylene oxide residue. According to disclosure of WO 97/17607 Triton X-100 is preferably present in the membrane in an amount of between 10 and 45% by weight.

Despite their hydrophilic regions, the above membranes display a rather slow glucose permeability and thus a rather long response time upon exposure to glucose-containing samples. The slow permeation across the swelled phase is ascribed to its high tortuousity, i.e. the high impedance to flow as caused by an increased effective path length. Accordingly, such membranes do not fulfill the demands of a fast permeability and short response time.

According to another approach outer membranes are microporous structures from polymers like polycarbonate, polypropylene and polyesters. The porosity of such membranes are provided by physical means, e.g. by neutron or argon track etching.

Glucose and oxygen permeate across such membranes in water-filled pores. Compared to the above membranes, however, the tortuousity of microporous membranes is lower, i.e. the effective pathlength is lower. Accordingly, microporous membrane provide shorter response times compared to the above membranes.

The precise control of the permeability properties of such microporous membranes is provided from subsequent chemical modifications. Examples of this type of membrane are:

U.S. Pat. No. 4,919,767 to Imperial Chemical Industries PLC of the United Kingdom which discloses a microporous polymer membrane which has been treated to at least partially fill the pores with a liquid of limited volatility which is not significantly soluble in water, e.g. an lipid like isopropyl myristate or an ester of a fatty acid like methyl oleate.

International patent application WO 97/36994 to Radiometer Medical A/S of Denmark which discloses a sensor with an outer membrane the surface of which is modified such that a hydrophilic component is immobilised on the surface in such manner that chains of the hydrophilic component are chemically bonded to free groups on the surface to provide said surface with a more hydrophilic character relative to its unmodified state. According to the disclosure of WO 97/36994 the membrane has free carboxylic or hydroxylic grouts on the surface. Upon modification the membrane pores are covered with hydrophilic chains, which support a fast glucose transport in the water-filled pores, and which by means of their "eelgrass"-like movements prevent macro-molecules from blocking surface and pores. Accordingly, the permeability properties of microporous membranes may be tailored to provide fast permeability and short response time.

Regrettably, the microporous membranes display insufficient adhesion to such polymer encapsulant structures as disclosed in international patent application No. WO 97/43634 to SenDx Medical Inc. of California, USA which may be used as substrate coatings of planar sensors.

Thus, despite the hitherto proposed membrane formulations there is still a need for a membrane for a sensor which display fast glucose permeability and thus short response time upon exposure to glucose-containing samples and which further show proper adhesion to polymer encapsulant structures of planar sensors such as disclosed in international patent application No. WO 97/43634 to SenDx Medical Inc. of California, USA.

This has been achieved by the membrane according to the invention comprising at least one polymer material, at least one surfactant and at least one hydrophilic compound in admixture.

According to the invention it has been found that the presence of at least one surfactant along with at least one hydrophilic compound allows an improved control of the membrane permeability characteristics.

Although not fully understood it is believed that the interaction between surfactant and hydrophilic compound provides a structure in which domains of hydrophilic compound are lined with surfactant molecules to produce micelles, and that such micelles are distributed in the polymer structure. The membrane is further believed to have a structure comprising a perculating network of pores lined with surfactant. The micelles are distributed in this network. Membranes of such structures display fast glucose permeability and proper adhesion to polymer encapsulant structures.

It should be understood that the at least one hydrophilic compound of the membrane is immiscible with the at least one polymer. Thus upon solvent evaporation the at least one hydrophilic compound is believed to produce hydrophilic domains which interact with the polymer only via the surfactant. In accordance herewith it is believed, that the at least one hydrophilic compound is present only in said micelles and at the membrane surface and that no hydrophilic compound is dissolved in the bulk polymers.

According to Hansen (Charles M. Hansen: Hansen Solubility Parameters—A User's Handbook, CRC Press (1999))
any solvent or polymer may be characterised by a set of solubility parameters $\delta_d$, $\delta_p$, and $\delta_h$ expressing the (atomic) dispersion forces, the (molecular) dipole interaction forces and the (molecular) hydrogen bonding forces contributing to the evaporation energy E, respectively, where $\delta_n=(E_n/V)^{1/2}$, V being the molar volume of the compound. Further, any polymer has a characteristic interaction radius $R_{o-pol}$, those solvents within a sphere of this radius being able to dissolve the polymer.

Thus, according to a preferred embodiment of the invention the at least one polymer is selected from those polymers of a solubility sphere of interaction radius=$R_{o-pol}$ and centered at the Hansen solubility parameters $\delta_{d-pol}$, $\delta_{p-pol}$, $\delta_{h-pol}$ the solubility sphere of which has a common volume segment with a sphere of radius=5.8 and centered at $\delta_d=18.1$, $\delta_p=7.0$, $\delta_h=6.0$, and the at least one hydrophilic compound is selected from those hydrophilic compounds the Hansen solubility parameters $\delta_{d-hydr}$, $\delta_{p-hydr}$, $\delta_{h-hydr}$ of which are excluded from the solubility sphere of the at least one polymer. The above parameters are the parameters of the preferred polymer polyvinyl chloride, and thus the above polymers are polymers, which have solubility characteristics similar to polyvinyl chloride.

Alternatively, the at least one polymer is selected from those polymers of a solubility sphere of interaction radius=$R_{o-pol}$ and centered at the Hansen solubility parameters $\delta_{d-pol}$, $\delta_{p-pol}$, $\delta_{h-pol}$ of which $\delta_{d-pol}$, $\delta_{p-pol}$, and $\delta_{h-pol}$ are included in a sphere of radius=5.8 and centered at $\delta_d=18.1$, $\delta_p=7.0$, $\delta_h=6.0$, and the at least one hydrophilic compound is selected from those hydrophilic compounds the Hansen solubility parameters $\delta_{d-hydr}$, $\delta_{p-hydr}$, $\delta_{h-hydr}$ of which are excluded from the solubility sphere of the at least one polymer.

Further alternatively, the at least one polymer is selected from those polymers of a solubility sphere of interaction radius=$R_{o-pol}$ and centered at the Hansen solubility parameters $\delta_{d-pol}$, $\delta_{p-pol}$, $\delta_{h-pol}$ the solubility sphere of which is included in a sphere of radius=5.8 and centered at $\delta_d=18.1$, $\delta_p=7.0$, $\delta_h=6.0$, and the at least one hydrophilic compound is selected from those hydrophilic compounds the Hansen solubility parameters $\delta_{d-hydr}$, $\delta_{p-hydr}$, $\delta_{h-hydr}$ of which are excluded from the solubility sphere of the at least one polymer.

Preferably the at least one polymer is selected from polyvinyl chlorides, polyvinylidene chlorides, polyvinylidene-acrylonitrile copolymers and their mixtures with butadiene-acrylonitrile copolymers, polyesters and UV-curable acrylates thereof, polycarbonates, glycol modified polyethylene terephthalates, polyacrylates, polymethacrylates, polystyrenes, polyurethanes and UV-curable acrylates thereof as well as UV-curable epoxy acrylates, more preferably polyvinyl chlorides, polyvinylidene chlorides, polyvinylidene-acrylonitrile copolymers and polyesters.

The at least one polymer is preferably present in an amount of between 70% and 99% by weight of the membrane.

According to a preferred embodiment of the invention the at least one hydrophilic compound is selected from those hydrophilic compounds the Hansen solubility parameters $\delta_{d-hydr}$, $\delta_{p-hydr}$, $\delta_{h-hydr}$ of which are excluded from a sphere of radius=5.8 and center at $\delta_d=18.1$, $\delta_p=7.0$, $\delta_h=6.0$.

In a further preferred embodiment of the invention the at least one hydrophilic compounds is selected from those hydrophilic compounds the Hansen solubility parameters $\delta_{d-hydr}$, $\delta_{p-hydr}$, $\delta_{h-hydr}$ of which are included in a sphere of radius=9.2 and of center at $\delta_d=16.6$, $\delta_p=12.0$, $\delta_h=20.7$. The above parameters are the parameters of the preferred hydrophilic compound diethylene glycol, and thus those hydrophilic compounds included in the above sphere are compounds, which have solubility characteristics similar to diethylene glycol.

Preferably the at least one hydrophilic compound is selected from the following groups of alcohols, glycols and ethers:

$C_2$–$C_4$ alcohols ethanol, propanol, isopropanol, butanol, isobutanol and t-butanol;

$C_2$–$C_4$ di- and trialcohols ethylene glycol, propylene glycol, 1,3-propanediol, 1,2-, 1,3- and 1,4-butanediol and glycerol;

polyethylene (2-8) glycol and polypropylene (2-3) glycol;

mono- and polyethylene (2-8) glycol and mono- and polypropylene (2-3) glycol monomethyl and monoethyl ether;

polyethylene (2-8) glycol dimethyl, diethyl and methylethyl diether.

More preferably the at least one hydrophilic compound is selected from diethylene glycol and triethylene glycol, diethylene glycol being the most preferred hydrophilic compound.

It should be understood, that the numerical denomination of e.g. polyethylene (2-8) glycol dimethyl denotes the range of the average number of repetitive units of the compounds.

In another preferred embodiment of the invention the at,least one hydrophilic compound is selected from mono- and poly-(2-4) saccharides.

It has been found that in the case where the at least one hydrophilic compound is present in an amount corresponding to between 1% and 20% by weight of the membrane excellent membrane properties are obtained.

It was further found, that those surfactants of a hydrophilic-hydrophobic balance (HLB) value less than 12, preferably less than 10 provide membranes which have particularly good properties. The HLB is defined as twenty times the molecular weight of the hydrophilic part of the surfactant relative to the full molecular weight of the surfactant.

In the case of the at least one hydrophilic compound being selected from alcohols, glycols and ethers the at least one surfactant is selected from the groups of:

polyethylene glycol fatty acid esters, preferably mono- and polyethylene (2-10) glycol laurates, myristates, palmitates, stearates and oleates;

polyethylene glycol ethers, preferably octyl, nonyl, decyl, dodecyl, tetradecyl, hexadecyl, octylphenyl, nonylphenyl, decylphenyl, dodecylphenyl, tetradecyl-phenyl and hexadecylphenyl ethers of polyethylene (2-10) glycol.

In a preferred embodiment of the invention the at least one surfactant is selected from polyethylene (3) glycol trimethylnonyl ether, polyethylene (4) glycol nonylphenyl ether and polyethylene (4) glycol lauryl ether.

Alternatively, in the case of the at least one hydrophilic compound being selected from saccharides the at least one surfactant is selected from the groups of:

saccharide fatty acid esters, preferably mono-, di- and poly-glucoside, methylglucoside, glucopyranoside and maltoside laurates, myristates, palmitates, stearates and oleates;

saccharide fatty ethers, preferably octyl, nonyl, decyl, dodecyl and tetradecyl mono-, di- and poly-glucosides, methylglucosides, glucopyranosides and maltosides;

the sorbitol fatty acid esters, preferably sorbitol and ethoxylated sorbitol laurates, myristates, palmitates, stearates and oleates.

The at least one surfactant is preferably present in amount of between 0.1% and 10% by weight of the membrane.

The membrane preferably has a thickness in the range 0.5–10 µm, more preferably 1–5 µm.

The invention further covers a method for the preparation of a sensor membrane.

According to this second aspect of the invention a sensor membrane is prepared by a method comprising the steps of mixing at least one polymer material, at least one surfactant, at least one hydrophilic compound and at least one solvent, subsequently applying said mixture onto a substrate and allowing the at least one solvent to evaporate.

The at least one polymer material, the at least one surfactant and the at least one hydrophilic compound according to the method are selected from those groups of polymer materials, surfactants and hydrophilic compounds described above. According to the invention the at least one polymer is soluble in the at least one solvent.

Thus, according to a preferred embodiment of the invention the at least one polymer is selected from those polymers of a solubility sphere of interaction radius=$R_{g\text{-}pol}$ and centered at the Hansen solubility parameters $\delta_{d\text{-}pol}$, $\delta_{p\text{-}pol}$, $\delta_{h\text{-}pol}$ the solubility sphere of which has a common volume segment with a sphere of radius=5.8 and centered at $\delta_d$=18.1, $\delta_p$=7.0, $\delta_h$=6.0, and the at least one solvent is selected from those solvents the Hansen solubility parameters $\delta_{d\text{-}sol}$, $\delta_{p\text{-}sol}$, $\delta_{h\text{-}sol}$ of which are included in the solubility sphere of the at least one polymer.

Alternatively, the at least one polymer is selected from those polymers of a solubility sphere of interaction radius=$R_{o\text{-}pol}$ and centered at the Hansen solubility parameters $\delta_{d\text{-}pol}$, $\delta_{p\text{-}pol}$, $\delta_{h\text{-}pol}$ of which $\delta_{d\text{-}pol}$, $\delta_{p\text{-}pol}$, and $\delta_{h\text{-}pol}$ are included in a sphere of radius=5.8 and centered at $\delta_d$=18.1, $\delta_p$=7.0, $\delta_h$=6.0, and the at least one solvent is selected from those solvents the Hansen solubility parameters $\delta_{d\text{-}sol}$, $\delta_{s\text{-}pol}$, $\delta_{s\text{-}pol}$ of which are included in the solubility sphere of the at least one polymer.

Further alternatively, the at least one polymer is selected from those polymers of a solubility sphere of interaction radius=$R_{o\text{-}pol}$ and centered at the Hansen solubility parameters $\delta_{d\text{-}pol}$, $\delta_{p\text{-}pol}$, $\delta_{h\text{-}pol}$ the solubility sphere of which is included in a sphere of radius=5.8 and centered at $\delta_d$=18.1, $\delta_p$=7.0, $\delta_h$=6.0, and the at least one solvent is selected from those solvents the Hansen solubility parameters $\delta_{d\text{-}sol}$, $\delta_{p\text{-}sol}$, $\delta_{h\text{-}sol}$ of which are included in the solubility sphere of the at least one polymer.

According to a preferred embodiment of the Invention the at least one solvent is selected from those solvents the Hansen solubility parameters $\delta_{d\text{-}sol}$, $\delta_{p\text{-}sol}$, $\delta_{h\text{-}sol}$ of which are included in a sphere of radius=5.8 and center at $\delta_d$=18.1, $\delta_p$=7.0, $\delta_h$=6.0.

Preferably the at least one solvent is selected from the groups of:

aliphatic $C_5$–$C_8$ alcohols pentanol, hexanol, heptanol and octanol;

alicyclic $C_5$–$C_8$ alcohols cyclopentanol, cyclohexanol, cycloheptanol and cyclooctanol;

aliphatic esters ethyl, propyl, isopropyl, butyl, isobutyl and t-butyl acetate, propionate and 2-hydroxy propionate;

alicyclic ethers tetrahydrofurane and 2-methyl tetrahydrofurane;

aliphatic ketones represented by the general formula $R_1$—C(=O)—$R_2$ wherein $R_1$ and $R_2$ independently represent methyl, ethyl, propyl and isopropyl and butyl, isobutyl and t-butyl;

alicyclic $C_5$–$C_8$ ketones cyclopentanone, cyclohexanone, cycloheptanone and cyclooctanone.

Most preferably the at least one solvent is selected from tetrahydrofurane and cyclohexanone.

The membrane forming mixture preferably has a composition of 70–99 parts per weight of polymer, 0.1–10 parts per weight of surfactant and 1–20 parts per weight hydrophilic compound and 900–9900 parts per weight of solvents.

According to this aspect the mixture is applied onto a polymer film, a glass or onto the enzyme layer of a layered structure of at least one electrode, an inner membrane and an enzyme layer using a solvent casting technique, e.g. a dispensing technique or a printing technique, e.g. a serigraphic technique.

Optionally, the method includes a conditioning step, in which the membrane is rinsed with an aqueous solution, preferably an aqueous solution of one or more salts and one or more surfactants. Although not fully understood it is believed that upon conditioning of the membrane a porous structure is formed as at least part of and optionally all of the at least one hydrophilic compound is washed out of the membrane structure. As illustrated below in FIGS. 3 and 4 it is thus believed that those micelles which are part of a perculating network of micelles contribute to the open porosity of the membrane.

A third aspect of the invention relates to a layered membrane structure for a sensor comprising a first membrane, an enzyme layer and a second membrane in which said first membrane is the membrane according to the first aspect of the invention or is a membrane prepared by the method according to the second aspect of the invention. The second membrane is selected from the groups of interference limiting membranes and ion selective membranes. In the case of the sensor being an amperometric sensor the second membrane is preferably an interference limiting membrane and in the case of the sensor being a potentiometric sensor the preferred membrane is an ion selective membrane.

In a preferred embodiment of the Invention the enzyme layer of the layered membrane structure comprises glucose oxidase, lactate oxidase, urease or enzymes for the oxidation of creatinine.

A fourth aspect of the invention relates to a sensor comprising a first membrane, an enzyme layer, optionally a second membrane and at least one electrode whereby said first membrane is the membrane according to the first aspect of the invention or whereby the said first membrane is a membrane prepared by the method according to the second aspect of the invention or whereby said first membrane, said enzyme layer and said optional second membrane provide a layered membrane structure which is the layered membrane structure according to the third aspect of the invention.

The first membrane is preferably an outer membrane, i.e. a membrane facing the sample and separating the sample and the enzyme layer.

Preferably, the sensor is equilibrated at a relative humidity of at most 30% and has a water content corresponding hereto.

The sensor is preferably a planar sensor.

In one embodiment the surface of the sensor facing the sample consists of the outer membrane of the present invention and a polymer encapsulant structure as described in international patent application no. WO 97/43634 to SenDx Medical Inc. of California, USA. According to this embodiment of the invention the membrane is bound to the polymer encapsulant.

The membrane, the layered membrane structure and the sensor according to the first, third and fourth aspects of the present invention are applicable for any analytical measurement which require controlled analyte permeability. Among others, such measurements include measurements of compounds in biological and physiological fluids such a blood, urine, cerebrospinal fluid, environmentally critical compounds or measurements of critical process parameters.

The at least one hydrophilic compound is preferably applied in an amount corresponding to between 1% and 20% by weight of the membrane. Compared thereto the open porosity of the membranes has been found to be in the range 0.1–3%. According to the applicants understanding of the membrane of the present invention it is thus believed that the major part of the hydrophilic compounds is In fact situated in non-perculating pores and on the membrane surface and thus not contributing to the open porosity.

The main role of the surfactant is believed to be the provision of a proper distribution of the hydrophilic compound in the polymer network, and the subsequent stabilisation of the membrane. Thus the surfactant is believed not to be a poreformer in itself.

Surprisingly it has been found, that those surfactants of a hydrophilic-hydrophobic balance (HLB) value less than 12, preferably less than 10, provide membranes which have particularly good permeability properties. It is believed that the low HLB surfactants are not dissolved upon membrane rinsing and thus not washed out of the membrane as may be the case with high HLB surfactants like Triton X-100.

The application of low HLB surfactants, on the other hand, has been possible only when combined with the hydrophilic compounds, which provides a controlled distribution of the surfactants. Accordingly, there is a true synergetic effect from the combined application of surfactants and hydrophilic compounds.

It should be understood, that the interaction between surfactant and hydrophilic compound is particularly synergetic in those cases, where the hydrophilic part of the at least one surfactant has structural similarities with the at least one hydrophilic compound.

Accordingly it has been found that particular good membrane properties are obtained in those cases where the at least one hydrophilic compound selected from the groups of alcohols, glycols and ethers is combined with the at least one surfactant including polyethylene glycol moieties.

Similarly it has been found that excellent membrane properties are obtained in those cases where the at least one hydrophilic compound selected from saccharides is combined with the group of surfactants of the saccharide fatty acid esters, saccharide fatty ethers and sorbitol fatty acid esters.

The solvents for the membrane preparation should allow the dissolution of the at least one polymer, however, at most be partly miscible with the at least one hydrophilic compound. In particular, the at least one polymer should be soluble only in the at least one solvent and not in the at least one hydrophilic compound. Thus, upon solvent evaporation, the molecules of the at least one hydrophilic compound should gather in the micelles and on the membrane surface to provide the requested structure.

It should be understood, that the at least one hydrophilic compound should show no or only little evaporation during the solvent evaporation.

In order to reduce permeability across the polymer bulk phase it has been found, that the polymers of the membranes of the present invention should either be operated below their glass transition temperature ($T_g$) or have a high degree of crystallinity. Thus polyvinyl chlorides, polyvinylidene chlorides, polyvinylidene chloride-acrylonitrile copolymers and polyesters which have $T_g$'s above 40° C. are the preferred polymers.

Figure 1:
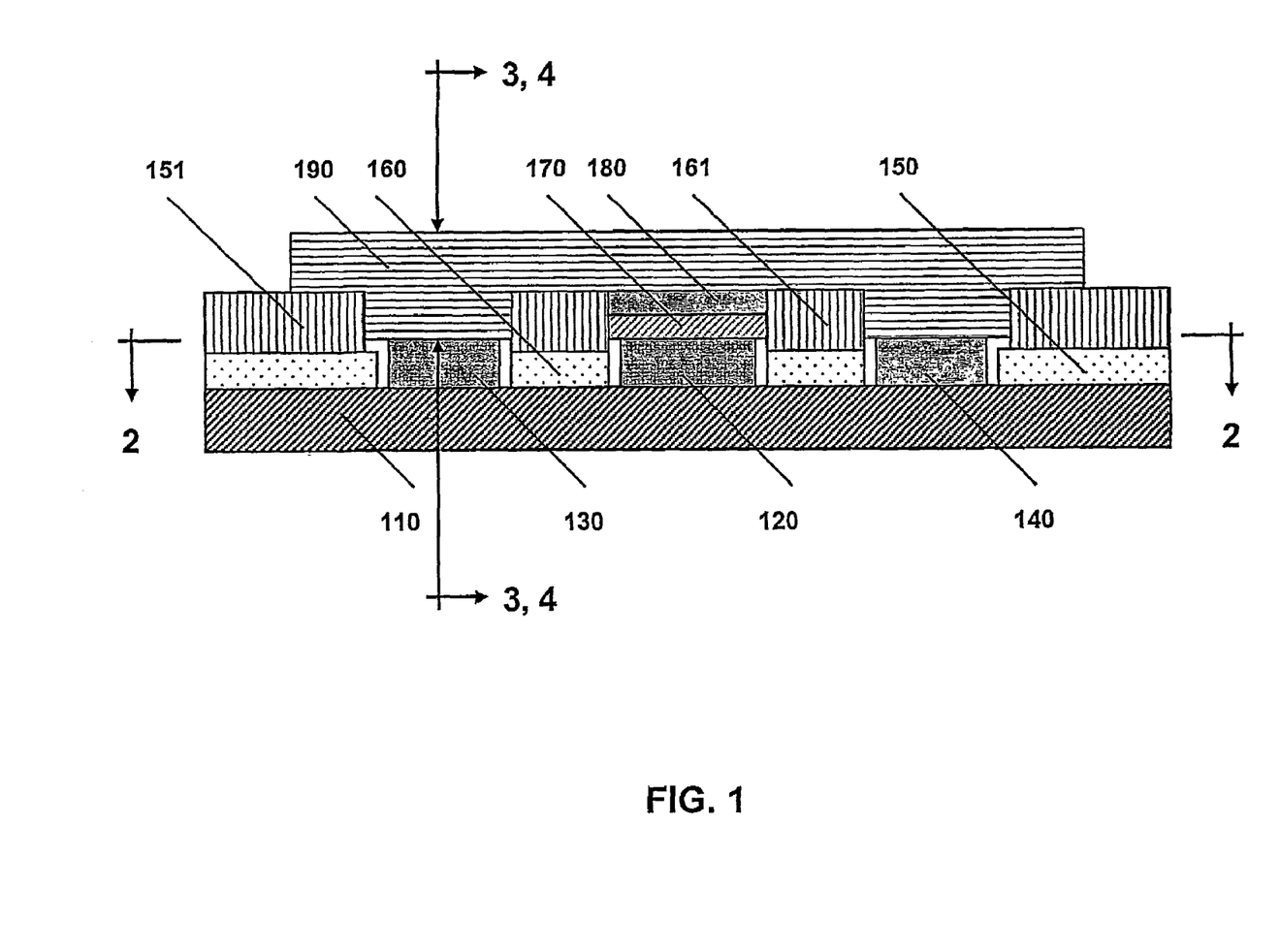
FIG. 1 is a schematic view of an electrochemical glucose sensor displaying the layered structure thereof.

Referring to FIG. 1 an alumina substrate 110 of a thickness of 200 μm is provided at one surface with a circular platinum working electrode 120 of a diameter 1000 μm and a thickness of 10 μm, an annular platinum counter electrode 130 of an outer diameter 3000 μm, an inner diameter 2000 μm and a thickness of 10 μm, covering the angular range 30–330° of the outer periphery of the working electrode, and a circular silver/silver chloride reference electrode 140 of a diameter 50 μm, positioned at the outer periphery of the working electrode at 0°. All of these three electrode structures are connected to the sensor electronics (not shown) across the alumina substrates 110 via platinum filed through holes (not shown) traversing the substrate. Upon operation, the working electrode 120 is polarised to +675 mV vs. the reference electrode 140.

Further on the alumina substrate 110 are two-layered structures of glass and polymer encapsulant. These two-layered structures include an annular structure 160, 161 of an outer diameter 1800 μm, an inner diameter 1200 μm and a thickness of 50 μm surrounding the working electrode 120 and a structure 150, 151 of a thickness 50 μm surrounding the complete electrode system. Both of these two-layered structures consist of an inner layer 150, 160 facing the alumina substrate 110 of ESL glass 4904 from ESL Europe of the United Kingdom of a thickness of 20 μm, and an outer layer 151, 161 of polymer encapsulant from SenDx Medical Inc. of California, USA as disclosed in international patent application WO97/43634 to SenDx Medical Inc. of California, USA which comprises 28.1% by weight of polyethylmethacrylate (Elvacite, part number 2041, from DuPont), 36.4% by weight of carbitol acetate, 34.3% by weight of silaninized kaolin (part number HF900 from Engelhard), 0.2% by weight of fumed silica and 1.0% by weight of trimethoxysilane.

A circular inner membrane 170 of cellulose acetate and cellulose acetate butyrate of a diameter 1200 μm and a thickness of 10 μm covers the working electrode 120.

A circular enzyme layer 180 of glucose oxidase crosslinked by glutaric aldehyde of a diameter 1200μm and a thickness of 2 μm covers the inner membrane 170.

The enzyme layer 180 was prepared by dispensing 0.4 μl of a buffered solution of glucose oxidase crosslinked by glutaric aldehyde on the cellulose acetate membrane 170. The enzyme layer was dried 30 min. at 37° C.

A circular outer membrane layer 190 of PVC/trimethyl-nonyl-triethylene glycol/diethylene glycol of a diameter 4000 μm and a thickness of 10 μm covers the complete electrode system, centered onto the working electrode 120.

The outer membrane was prepared from 1.35 gram of poly vinyl chloride (Aldrich 34,676-4), 0.0149 gram of trimethylnonyl-triethylene glycol (Tergitol TMN3 from Th. Goldschmidt) and 0.134 gram diethylene glycol which were added to 21.3 gram of tetrahydrofurane and 7.58 gram of cyclohexanone. The mixture was stirred until the PVC was dissolved and a homogenous solution was obtained. 28.5 gram of tetrahydrofurane was added to obtain a 2% solution of a 90/1/9 PVC/surfactant/hydrophilic compound composition. The solution was dispensed on the sensor area to cover all three electrodes and to have an approx. 0.5 mm overlap with the polymer encapsulant 151. The outer membranes were dried for 30 min. at 23±2° C. and for 1½ hour at 40° C.

All three layers 170, 180, 190 were dispensed on an x,y,z-table mounted with an automatic dispensing unit (IVEK pump).

Figure 2:
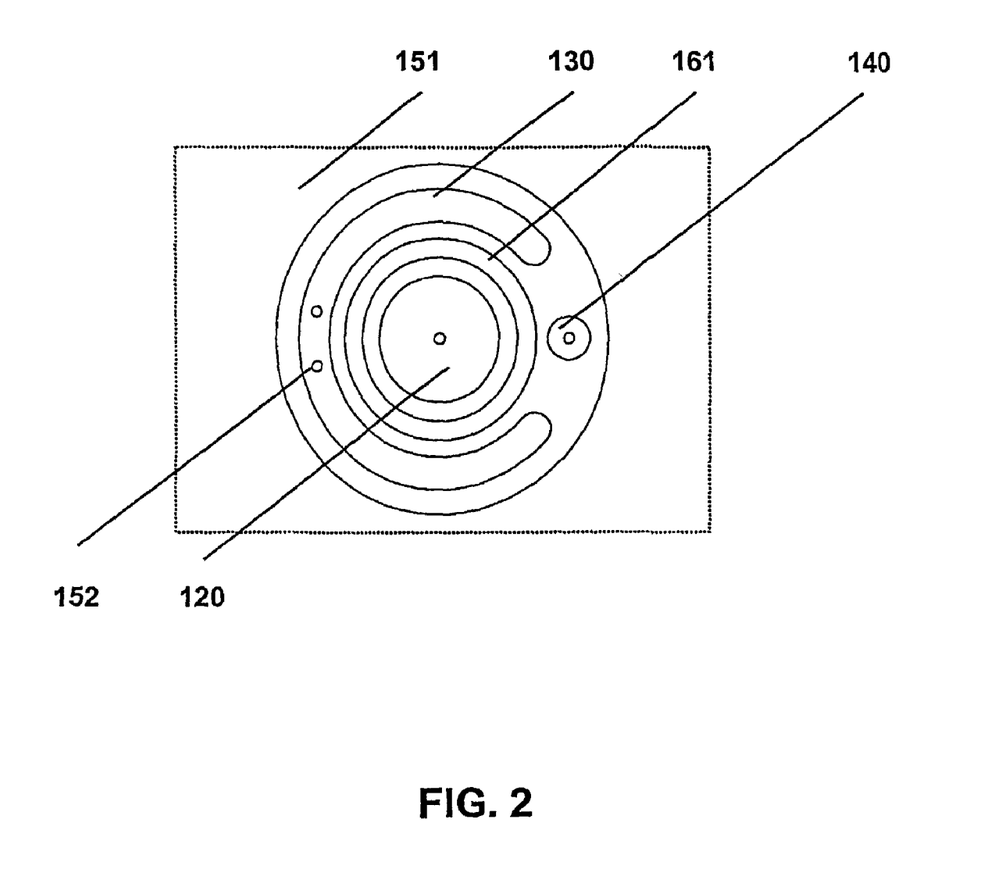
FIG. 2 is a sectional view of the electrodes and the polymer encapsulant structures of the sensor shown in FIG. 1.

Referring to FIG. 2 a sectional view of the electrodes and polymer encapsulant of FIG. 1 is shown, including the working electrode 120, the counter electrode 130, the reference electrode 140, the polymer encapsulant structures 151, 161 and platinum filed through holes 152 for electrical connection of the electrodes to the sensor electronics.

Figure 3:
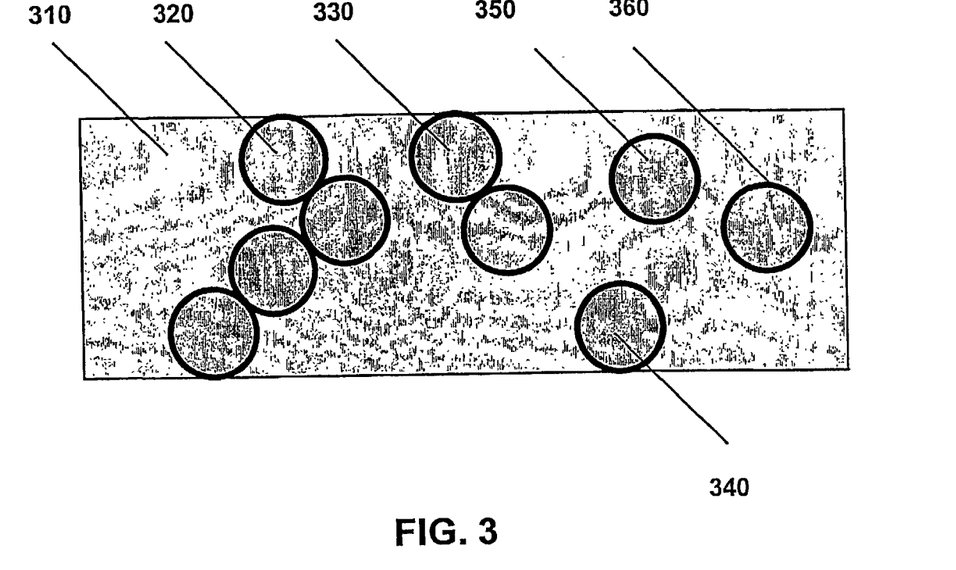
FIG. 3 is a sectional view of the structure of the membrane of the present invention prior to conditioning.

Referring to FIG. 3 a cross section of the unconditioned outer membrane of FIG. 1 shows the polymer matrix 310 including micelles of hydrophilic compound 320, 330, 340, 350. 320 represent micelles which are part of a perculating network, 330 representing micelles of a non-perculating network, however, reaching the membrane surface, 340 representing single micelles reaching the surface and 350 representing isolated micelles. The micelles are lined with surfactant 360, which also lines the membrane surface.

Figure 4:
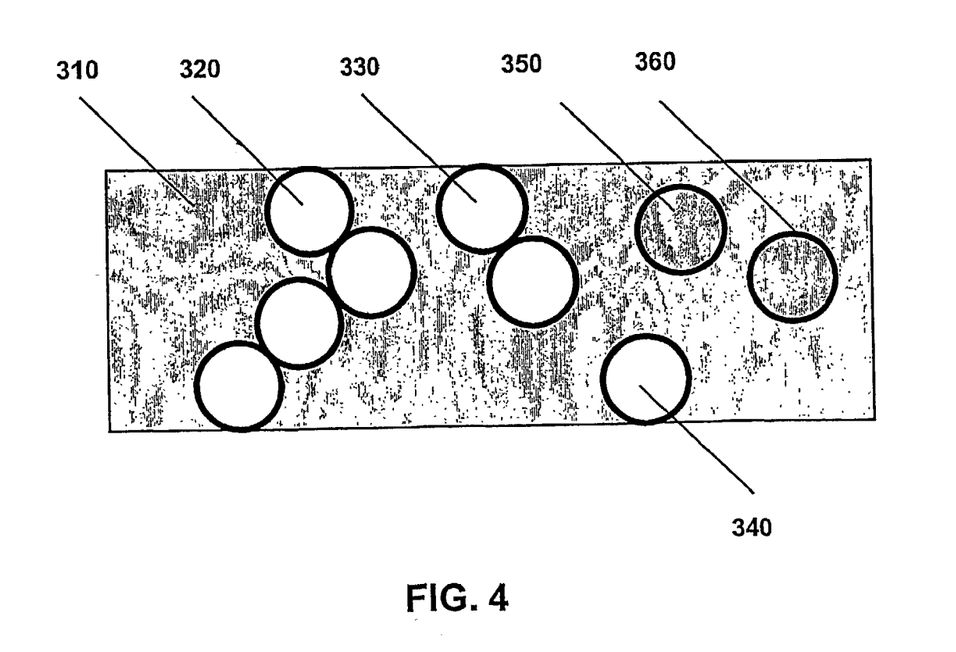
FIG. 4 is a sectional view of the structure of the conditioned membrane of the present invention.

Referring to FIG. 4 a similar cross section of the conditioned outer membrane of FIGS. 1 and 3 shows the micelles of perculating 320, non-perculating network 330 and single micelles at the membrane surface 340 which, upon rinsing with an aqueous solution of salts and surfactants, are converted to water-filled pores. The Isolated micelles 350 are unchanged upon such conditioning.

Figure 5:
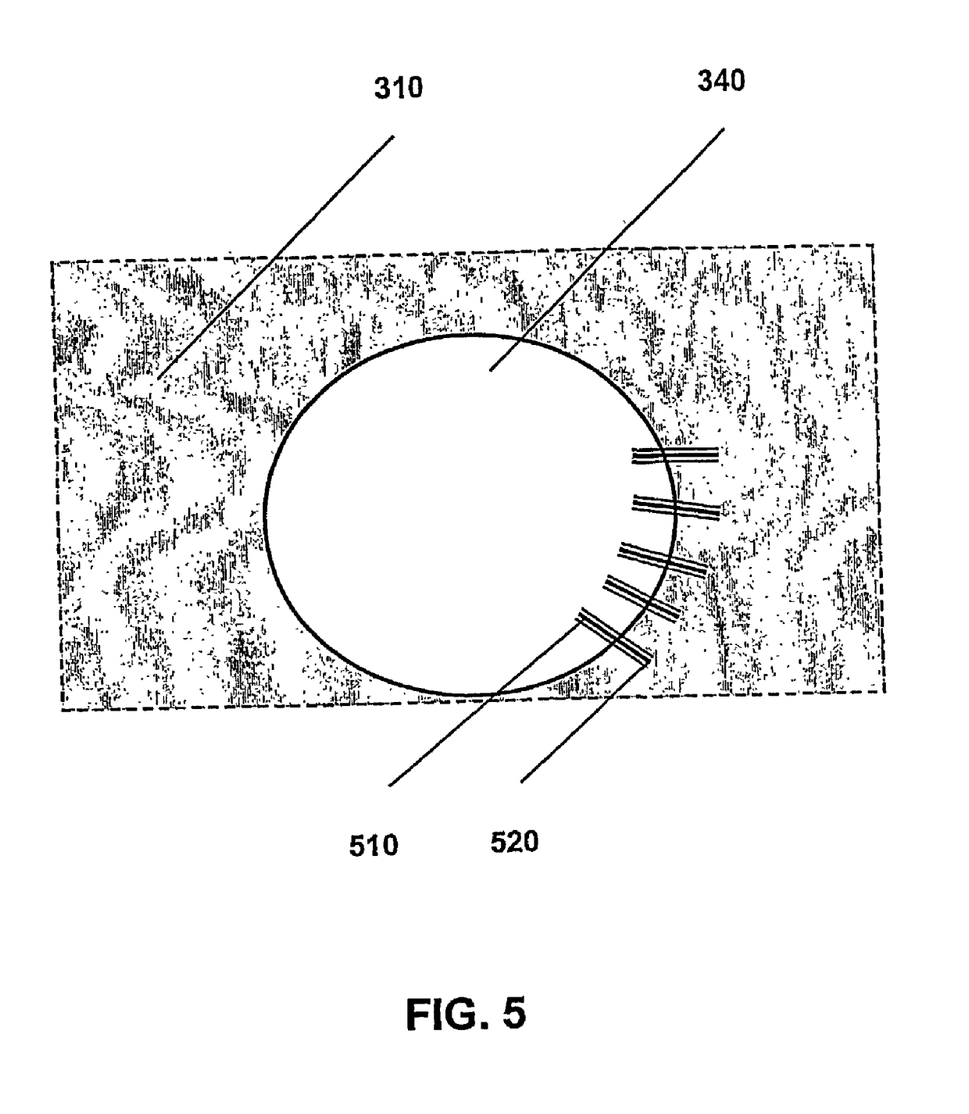
FIG. 5 is a schematic view of the structure of the pore surface of the conditioned membrane.

Referring to FIG. 5 a magnification of the pore 340 of FIG. 4 is shown. The surface of the water-filled pore is lined with surfactant molecules 360, the hydrophilic moieties of which 510 face the aqueous phase inside the pore and the hydrophobic moieties of which 520 face the bulk polymer.

Figure 6:
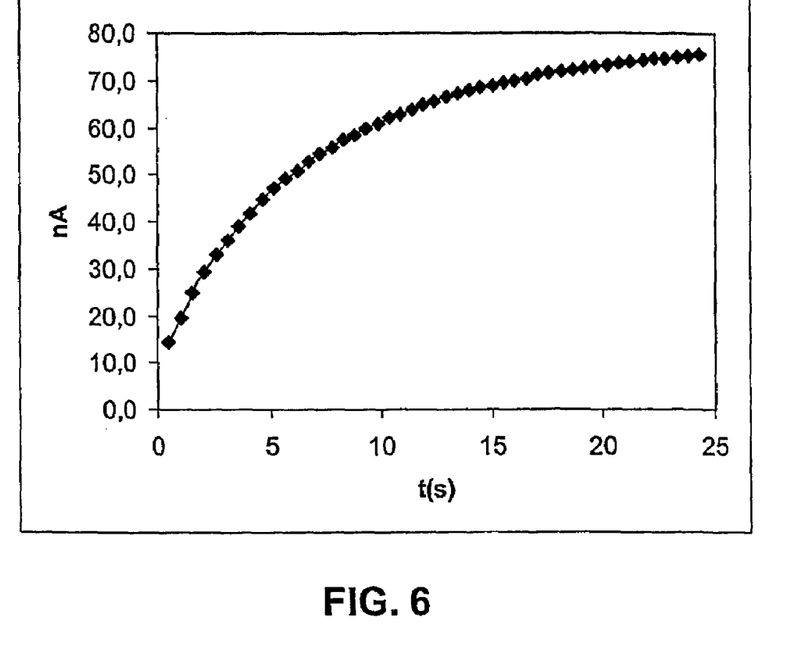
FIG. 6 illustrates the response curve of the sensor of FIG. 1.

Referring to FIG. 6 the response curve of the sensor of FIG. 1 is shown upon exposure to a solution of a glucose concentration of 30 mM at t=0 s. The response time for obtaining a signal of 50% of the equilibrium signal is 3 seconds. The response time for obtaining a signal of 80% of the equilibrium signal is 10 seconds, and both of these non-equilibrium signals allow simple and precise estimation of the equilibrium glucose concentration. Similar results were obtained upon exposing the sensor to solutions of glucose concentrations of 0, 1, 2, 5, 10 and 20 mM, respectively.

Figure 7:
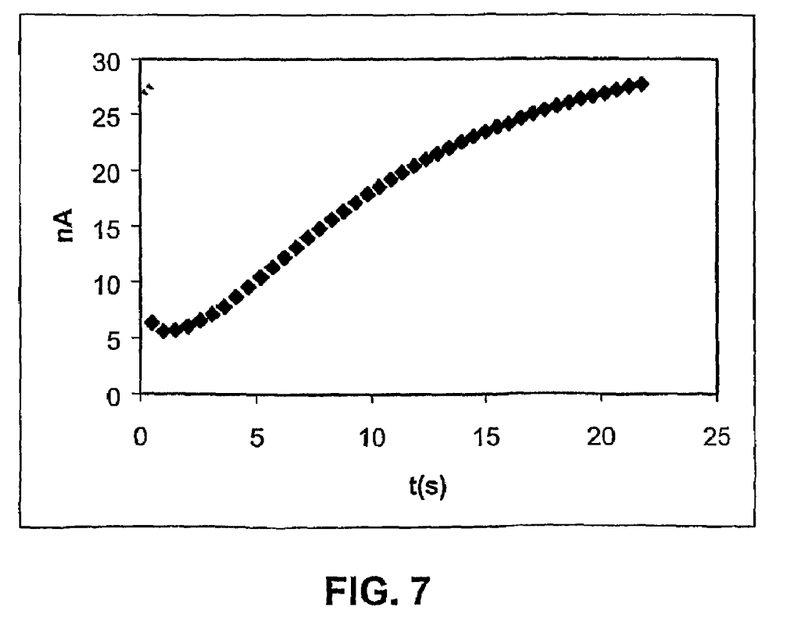
FIG. 7 illustrates the response curve of a sensor based on a prior art outer membrane.

FIG. 7 shows the response upon exposure to 30 mM glucose of a prior art sensor fabricated following the procedure of FIG. 1, however, substituting a mixture of 1 gram of PVC and 0.45 gram of Triton X-100 for the PVC/surfactant/hydrophilic compound composition of FIG. 1, thus corresponding to a disclosure on membrane composition of international patent application WO 97/17607. The response time for obtaining a signal of 50% of the equilibrium signal is 7 seconds. The response time for obtaining a signal of 80% of the equilibrium signal is 13 seconds. The response curve, does not allow the simple estimation of the equilibrium glucose concentration as does the response curve shown in FIG. 6. Similar results were obtained upon exposing the sensor to solutions of glucose concentrations of 0, 1, 2, 5, 10 and 20 mM, respectively.

As the typical response time of a sensor to paracetamol, e.g. of a concentration of 2 mM, is in the range 10–30s, paracetamol will affect the measurements of the prior art sensors whereas the influence on the sensor according to the present invention will be negligible.

For further comparison purposes, a sensor was fabricated following the procedure of FIG. 1, however, substituting a microporous polyester membrane as disclosed in international patent application No. WO 97/36994 to Radiometer Medical A/S of Denmark for the outer membrane of FIG. 1. The polyester membrane was fixed onto the polymer encapsulant using an epoxy resin.

This sensor did not respond at all, probably due to poor membrane conditioning, i.e. poor penetration of aqueous samples into the membrane to establish contact to the electrodes of the sensor.

As will be obvious, the above figures and examples are non-limiting in that the invention is not restricted to the embodiments of the figures and examples which are illustrative only.

The invention claimed is:

1. A sensor membrane comprising, in admixture, at least one polymer material, at least one hydrophilic compound, which is selected from the group consisting of polyethylene (2-8) glycol and polypropylene (2-3) glycol, and at least one surfactant, which has a hydrophilic-lipophilic balance (HLB) value less than 10 and which is selected from the group consisting of polyethylene glycol fatty acid esters and polyethylene glycol ethers.

2. A membrane according to claim 1 in which the at least one polymer is selected from those polymers of a solubility sphere of interaction radius $=R_{o\text{-}pol}$, and centered at the Hansen solubility parameters $\delta_{d\text{-}pol}$, $\delta_{p\text{-}pol}$, $\delta_{h\text{-}pol}$ the solubility sphere of which has a common volume segment with a sphere of interaction radius $=5.8$ and centered at $\delta_{d\text{-}pol}=18.1$, $\delta_{d\text{-}pol}=7.0$, $\delta_{h\text{-}pol}=6.0$, wherein $\delta_d$, $\delta_p$, $\delta_h$ represent solubility parameters expressing atomic dispersion forces, molecular dipole interaction forces, and molecular hydrogen bonding forces, respectively, and the solubility parameters for the polymer are designated $_{\text{-}pol}$.

3. A membrane according to claim 1 in which the at least one polymer is selected from those polymers of a solubility sphere of interaction radius $=R_{o\text{-}pol}$ and centered at the Hansen solubility parameters $\delta_{d\text{-}pol}$, $\delta_{p\text{-}pol}$, $\delta_{h\text{-}pol}$ of which $\delta_{d\text{-}pol}$, $\delta_{p\text{-}pol}$, and $\delta_{h\text{-}pol}$ are included in a sphere of interaction radius $=5.8$ and centered at $\delta_{d\text{-}pol}=18.1$, $\delta_{h\text{-}pol}=7.0$, $\delta_{h\text{-}pol}=6.0$, wherein $\delta_d$, $\delta_p$, and $\delta_h$ represent solubility parameters expressing atomic dispersion forces, molecular dipole interaction forces, and molecular hydrogen bonding forces, respectively, and the solubility parameters for the polymer are designated $_{\text{-}pol}$.

4. A membrane according to claim 1 in which the at least one polymer is selected from those polymers of a solubility sphere of interaction radius $=R_{o\text{-}pol}$, and centered at the Hansen solubility parameters $\delta_{d\text{-}pol}$, $\delta_{p\text{-}pol}$, $\delta_{h\text{-}pol}$ the solubility sphere of which is included in a sphere of interaction radius $=5.8$ and centered at $\delta_{d\text{-}pol}=18.1$, $\delta_{p\text{-}pol}=7.0$, $\delta_{h\text{-}pol}=6.0$, wherein $\delta_d$, $\delta_p$, and $\delta_h$ represent solubility parameters expressing atomic dispersion forces, molecular dipole interaction forces, and molecular hydrogen bonding forces, respectively, and the solubility parameters for the polymer are designated $_{\text{-}pol}$.

5. A membrane according to claim 1 in which the at least one polymer is selected from the group consisting of polyvinyl chlorides, polyvinylidene chlorides, polyvinylidene-acrylonitrile copolymers and their mixtures with butadiene-acrylonitrile copolymers, polyesters and UV-curable acrylates thereof, polycarbonates, glycol modified polyethylene terephthalates, polyacrylates, polymethacrylates, polystyrenes, polyurethanes and UV-curable acrylates thereof and UV-curable epoxy acrylates.

6. A membrane according to claim 1 in which the at least one polymer is present in an amount of between 70% and 99% by weight of the membrane.

7. A membrane according to claim 1 in which the at least one hydrophilic compound is present in an amount of 1–20% by weight of the membrane.

8. A membrane according to claim 1 in which the at least one surfactant is selected from the group consisting of polyethylene (3) glycol trimethylnonyl ether, polyethylene (4) glycol nonylphenyl ether and polyethylene (4) glycol lauryl ether wherein the numbers in parenthesis denote the range of the average number of repetitive units of the compound.

9. A membrane according to claim 1 in which the at least one surfactant is present in an amount of 0.1–10% by weight of the membrane.

10. A membrane according to claim 1 in which the membrane has a thickness in the range 0.5–10 μm.

11. A membrane according to claim 1 in which the membrane has a structure comprising micelles of hydrophilic compound lined with surfactant randomly distributed in the membrane bulk polymer.

12. A membrane according to claim 1 in which the membrane has a structure comprising a perculating network of pores lined with surfactant and isolated micelles of hydrophilic compound lined with surfactant.

13. A layered membrane structure for a sensor comprising a first membrane, an enzyme layer and a second membrane in which said first membrane is a membrane as described in claim 1.

14. A layered membrane structure according to claim 13 in which the enzyme layer comprises glucose oxidase, lactate oxidase, urease or enzymes for the oxidation of creatinine.

15. A layered membrane structure according to claim 13 in which said second membrane is selected from the group consisting of interference limiting membranes and ion selective membranes.

16. A sensor comprising a first membrane, an enzyme layer, and at least one electrode in which said first membrane and said enzyme layer provide a layered membrane structure as described claim 13.

17. A sensor according to claim 16 in which said first membrane is an outer membrane.

18. A sensor according to claim 17 in which the surface of the sensor facing the sample comprises the outer membrane and a polymer encapsulant structure.

19. A sensor according to claim 18 in which the outer membrane is bound to the polymer encapsulant structure.

20. A sensor according claim 16 in which the sensor is equilibrated at a relative humidity of at most 30% and has a water content corresponding hereto.

21. A sensor according to claim 16 in which the sensor is a planar sensor.

22. A sensor comprising a first membrane, an enzyme layer, and at least one electrode in which said first membrane is a membrane as described in claim 1.

23. A sensor according to claim 22 in which said first membrane is an outer membrane.

24. A sensor according to claim 23 in which the surface of the sensor facing the sample comprises the outer membrane and a polymer encapsulant structure.

25. A sensor according to claim 24 in which the outer membrane is bound to the polymer encapsulant structure.

26. A sensor according to claim 22 in which the sensor is equilibrated at a relative humidity of at most 30% and has a water content corresponding hereto.

27. A sensor according to claim 22 in which the sensor is a planar sensor.

28. A sensor membrane according to claim 1 in which the at least one polymer material is selected from polyvinyl chlorides, polyvinylidene chlorides, polyvinylidene-acetonitrile copolymers and polyesters.

29. A sensor membrane according to claim 1 in which the at least one polymer material is polyvinyl chloride, the at least one hydrophobic compounds is diethylene glycol and the at least one surfactant is trimethylnonyltriethylene glycol.

30. A method for the preparation of a sensor membrane comprising the steps of:
mixing at least one polymer material, at least one surfactant, at least one hydrophilic compound, which is selected from the group consisting of polyethylene (2-8) glycol and polypropylene (2-3) glycol, and at least one solvent in which the at least one polymer material is soluble
applying said mixture onto a substrate, and
evaporating the solvent wherein the at least one surfactant has a hydrophilic-lipophilic balance (HLB) value less than 10 and is selected from the group consisting of polyethylene cilycol fatty acid esters and polyethylene cilycol ethers.

31. A method according to claim 30 in which the at least one polymer is selected from those polymers of a solubility sphere of interaction radius $=R_{o\text{-}pol}$ and centered at the Hansen solubility parameters $\delta_{d\text{-}pol}$, $\delta_{p\text{-}pol}$, $\delta_{h\text{-}pol}$ the solubility sphere of which has a common volume segment with a sphere of interaction radius $=5.8$ and centered at $\delta_{d\text{-}pol}=18.1$, $\delta_{d\text{-}pol}=7.0$, $\delta_{h\text{-}pol}=6.0$, wherein $\delta_d$, $\delta_p$, and $\delta_h$ represent solubility parameters expressing atomic dispersion forces, molecular dipole interaction forces, and molecular hydrogen bonding forces, respectively, and the solubility parameters for the polymer are designated $_{\text{-}pol}$.

32. A method according to claim 30 in which the at least one polymer is selected from those polymers of a solubility sphere of interaction radius $=R_{o\text{-}pol}$ and centered at the Hansen solubility parameters $\delta_{d\text{-}pol}$, $\delta_{p\text{-}pol}$, $\delta_{h\text{-}pol}$ of which $\delta_{d\text{-}pol}$, $\delta_{p\text{-}pol}$, and $\delta_{h\text{-}pol}$ are included in a sphere of interaction radius 5.8 and centered at $\delta_{d\text{-}pol}=18.1$, $\delta_{h\text{-}pol}=7.0$, $\delta_{h\text{-}pol}=6.0$, wherein $\delta_d$, $\delta_p$, and $\delta_h$ represent solubility parameters expressing atomic dispersion forces, molecular dipole interaction forces, and molecular hydrogen bonding forces, respectively, and the solubility parameters for the polymer are designated $_{\text{-}pol}$.

33. A method according to claim 30 in which the at least one polymer is selected from those polymers of a solubility sphere of interaction radius $=R_{o\text{-}pol}$, and centered at the Hansen solubility parameters $\delta_{d\text{-}pol}$, $\delta_{p\text{-}pol}$, $\delta_{h\text{-}pol}$ the solubility sphere of which is included in a sphere of interaction radius $=5.8$ and centered at $\delta_{d\text{-}pol}=18.1$, $\delta_{p\text{-}pol}=7.0$, $\delta_{h\text{-}pol}=6.0$, wherein $\delta_d$, $\delta_p$, and $\delta_h$ represent solubility parameters expressing atomic dispersion forces, molecular dipole interaction forces, and molecular hydrogen bonding forces, respectively, and the solubility parameters for the polymer are designated $_{\text{-}pol}$.

34. A method according to claim 30 in which the at least one polymer is selected from the group consisting of polyvinyl chlorides, polyvinylidene chlorides, polyvinylidene-acrylonitrile copolymers and their mixtures with butadiene-acrylonitrile copolymers, polyesters and UV-curable acrylates thereof, polycarbonates, glycol modified polyethylene terephthalates, polyacrylates, polymethacrylates, polystyrenes, polyurethanes and UV-curable acrylates thereof and UV-curable epoxy acrylates.

35. A method according to claim 30 in which the at least one hydrophilic compound is selected from the group consisting of diethylene glycol and triethylene glycol.

36. A method according to claim 30 in which the at least one surfactant is selected from the group consisting of polyethylene (3) glycol trimethylnonyl ether, polyethylene (4) glycol nonylphenyl ether and polyethylene (4) glycol lauryl ether wherein the numbers in parenthesis denote the range of the average number of repetitive units of the compound.

37. A method according to claim 30 in which the at least one polymer is selected from those polymers of a solubility sphere of interaction radius $=R_{o\text{-}pol}$ and centered at the Hansen solubility parameters $\delta_{d\text{-}pol}$, $\delta_{p\text{-}pol}$, $\delta_{h\text{-}pol}$ the solubility sphere of which has a common volume segment with a sphere of interaction radius $=5.8$ and centered at $\delta_{d\text{-}pol}=18.1$, $\delta_{p\text{-}pol}=7.0$, $\delta_{h\text{-}pol}=6.0$, and in which the at least one solvent is selected from those solvents for which all of the Hansen solubility parameters $\delta_{d\text{-}sol}$, $\delta_{p\text{-}sol}$, $\delta_{h\text{-}sol}$ are included in the solubility sphere of the at least one polymer, wherein $\delta_d$, $\delta_p$, and $\delta_h$ represent solubility parameters expressing atomic dispersion forces, molecular dipole interaction forces, and molecular hydrogen bonding forces, respectively, and the solubility parameters for the polymer are designated $_{\text{-}pol}$ and the solubility parameters for the solvent compound are designated $_{\text{-}sol}$.

38. A method according to claim 30 in which the at least one polymer is selected from those polymers of a solubility sphere of interaction radius $=R_{o\text{-}pol}$ and centered at the Hansen solubility parameters $\delta_{d\text{-}pol}$, $\delta_{p\text{-}pol}$, $\delta_{h\text{-}pol}$ of which $\delta_{d\text{-}pol}$, $\delta_{p\text{-}pol}$, and $\delta_{h\text{-}pol}$ are included in a sphere of interaction radius $=5.8$ and centered at $\delta_{d\text{-}pol}=18.1$, $\delta_{p\text{-}pol}=7.0$, $\delta_{h\text{-}pol}=6.0$, and in which the at least one solvent is selected from those solvents for which all of the Hansen solubility parameters $\delta_{d\text{-}sol}$, $\delta_{p\text{-}sol}$, $\delta_{h\text{-}sol}$ are included in the solubility sphere of the at least one polymer, wherein $\delta_d$, $\delta_p$, and $\delta_h$ represent solubility parameters expressing atomic dispersion forces, molecular dipole interaction forces, and molecular hydrogen bonding forces, respectively, and the solubility parameters for the polymer are designated $_{\text{-}pol}$ and the solubility parameters for the solvent compound are designated $_{\text{-}sol}$.

39. A method according to claim 30 in which the at least one polymer is selected from those polymers of a solubility sphere of interaction radius $=R_{o\text{-}pol}$, and centered at the Hansen solubility parameters $\delta_{d\text{-}pol}$, $\delta_{p\text{-}pol}$, $\delta_{h\text{-}pol}$ the solubility sphere of which is included in a sphere of interaction radius $=5.8$ and centered at $\delta_{d\text{-}pol}=18.1$, $\delta_{p\text{-}pol}=7.0$, $\delta_{h\text{-}pol}=6.0$, and in which the at least one solvent is selected from those solvents for which all of the Hansen solubility parameters $\delta_{d\text{-}sol}$, $\delta_{p\text{-}sol}$, $\delta_{h\text{-}sol}$ are included in the solubility sphere of the at least one polymer, wherein $\delta_d$, $\delta_p$, and $\delta_h$ represent solubility parameters expressing atomic dispersion forces, molecular dipole interaction forces, and molecular hydrogen bonding forces, respectively, and the solubility parameters for the polymer are designated $_{\text{-}pol}$ and the solubility parameters for the solvent compound are designated $_{\text{-}sol}$.

40. A method according to claim 30 in which the at least one solvent is selected from those solvents the in which all of the Hansen solubility parameters $\delta_{d\text{-}sol}$, $\delta_{p\text{-}sol}$, $\delta_{h\text{-}sol}$ are included in a sphere of radius =5.8 and centered at $\delta_{d\text{-}sol}$=18.1, $\delta_{p\text{-}sol}$=7.0, $\delta_{h\text{-}sol}$=6.0, wherein $\delta_{d\text{-}sol}$, $\delta_{p\text{-}sol}$, and $\delta_{h\text{-}sol}$ represent solubility parameters expressing atomic dispersion forces, molecular dipole interaction forces, and molecular hydrogen bonding forces, respectively, for the solvent.

41. A method according to claim 30 in which the at least one solvent is selected from the group consisting of:
aliphatic $C_5$–$C_8$ alcohols pentanol, hexanol, heptanol and octanol;
alicyclic $C_5$–$C_8$ alcohols cyclopentanol, cyclohexanol, cycloheptanol and cyclooctanol;
aliphatic esters ethyl-, propyl-, isopropyl, butyl, isobutyl and t-butyl acetate, propionate and 2-hydroxy propionate;
alicyclic ethers tetrahydrofurane and 2-methyl tetrahydrofurane;
aliphatic ketones represented by the general formula $R_1$—C(=O)—$R_2$ wherein $R_1$ and $R_2$ independently represent methyl, ethyl, propyl and isopropyl and butyl, isobutyl and t-butyl; and
alicyclic $C_5$–$C_8$ ketones cyclopentanone, cyclohexanone, cycloheptanone and cyclooctanone.

42. A method according to claim 41 in which the at least one solvent is selected from tetrahydrofurane and cyclohexanone.

43. A method according to claim 30 in which the mixture comprises 70–99 parts per weight of polymer, 1–20 parts per weight of hydrophilic compound, 0.1–10 parts per weight of surfactant and 900–9900 parts per weight of solvent.

44. A method according to claim 30 in which the application of the mixture onto a substrate is performed using a solvent casting technique.

45. A method according to claim 30 in which the application of the mixture onto a substrate is performed using a printing technique.

46. A method according to claim 30 in which the substrate for the application of the mixture is a polymer foil or a glass.

47. A method according to claim 30 in which the substrate for the application of the mixture is an enzyme layer of a sensor.

48. A method according to claim 30 further comprising a membrane conditioning step, in which the membrane conditioning step is a rinsing with an aqueous solution.

49. A layered membrane structure for a sensor comprising a first membrane, an enzyme layer and a second membrane in which the said first membrane is prepared by a method comprising the steps of:
mixing at least one polymer material, at least one surfactant, at least one hydrophilic compound, which is selected from the group consisting of polyethylene (2-8) glycol and polypropylene (2-3) glycol, and at least one solvent in which the at least one polymer material is soluble
applying said mixture onto a substrate, and
evaporating the solvent
wherein the at least one surfactant has a hydrophilic-lipophilic balance (HLB) value less than 10 and is selected from the group consisting of polyethylene glycol fatty acid esters and polyethylene glycol ethers.

50. A layered membrane structure according to claim 49 in which the enzyme layer comprises glucose oxidase, lactate oxidase, urease or enzymes for the oxidation of creatinine.

51. A layered membrane structure according to claim 50 in which said second membrane is selected from the group consisting of interference limiting membranes and ion selective membranes.

52. A sensor comprising a first membrane, an enzyme layer, and at least one electrode in which said first membrane and said enzyme layer provide a layered membrane structure as described in claim 49.

53. A sensor according to claim 52 in which said first membrane is an outer membrane.

54. A sensor according to claim 53 in which the surface of the sensor facing the sample comprises the outer membrane and a polymer encapsulant structure.

55. A sensor according to claim 54 in which the outer membrane is bound to the polymer encapsulant structure.

56. A sensor according to claim 52 in which the sensor is equilibrated at a relative humidity of at most 30% and has a water content corresponding hereto.

57. A sensor according to claim 52 in which the sensor is a planar sensor.

58. A sensor comprising a first membrane, an enzyme layer, and at least one electrode in which the said first membrane is a membrane prepared by a method comprising the steps of:
mixing at least one polymer material, at least one surfactant, at least one hydrophilic compound, which is selected from the group consisting of polyethylene (2-8) glycol and polypropylene (2-3) glycol, and at least one solvent in which the at least one polymer material is soluble
applying said mixture onto a substrate, and
evaporating the solvent
wherein the at least one surfactant has a hydrophilic-lipophilic balance (HLB) value less than 10 and is selected from the group consisting of polyethylene glycol fatty acid esters and polyethylene glycol ethers.

59. A sensor according to claim 58 in which said first membrane is an outer membrane.

60. A sensor according to claim 59 in which the surface of the sensor facing the sample comprises the outer membrane and a polymer encapsulant structure.

61. A sensor according to claim 60 in which the outer membrane is bound to the polymer encapsulant structure.

62. A sensor according to claim 58 in which the sensor is equilibrated at a relative humidity of at most 30% and has a water content corresponding hereto.

63. A sensor according to claim 58 in which the sensor is a planar sensor.

64. A sensor membrane comprising, in admixture, at least one polymer material, at least one hydrophilic compound, which is selected from the group consisting of diethylene glycol and triethylene glycol, and at least one surfactant, which has a hydrophilic-lipophilic balance (HLB) value less than 10 and which is selected from the group consisting of polyethylene glycol fatty acid esters and polyethylene glycol ethers.

* * * * *